(12) United States Patent
De Boni et al.

(10) Patent No.: US 7,976,584 B2
(45) Date of Patent: Jul. 12, 2011

(54) DYEING COMPOSITION COMPRISING A DYE AND A PROPYLENE GLYCOL DERIVATIVE

(75) Inventors: Maxime De Boni, Paris (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 110 days.

(21) Appl. No.: 11/919,221

(22) PCT Filed: Apr. 27, 2006

(86) PCT No.: PCT/FR2006/000953
§ 371 (c)(1),
(2), (4) Date: Sep. 10, 2008

(87) PCT Pub. No.: WO2006/114529
PCT Pub. Date: Nov. 2, 2006

(65) Prior Publication Data
US 2009/0165222 A1    Jul. 2, 2009

Related U.S. Application Data

(60) Provisional application No. 60/678,205, filed on May 6, 2005.

(30) Foreign Application Priority Data

Apr. 27, 2005  (FR) ...................... 05 51084

(51) Int. Cl.
*A61Q 5/10*    (2006.01)

(52) U.S. Cl. ............. 8/405; 8/406; 8/407; 8/408; 8/410; 8/412; 8/426; 8/435; 8/466; 8/552

(58) Field of Classification Search ............. 8/405, 406, 8/407, 408, 410, 412, 426, 435, 466, 552
See application file for complete search history.

(56) References Cited

U.S. PATENT DOCUMENTS 6,106,577 A * 8/2000 Audousset et al. ............... 8/403
6,602,303 B2 * 8/2003 Laurent et al. .................... 8/405

FOREIGN PATENT DOCUMENTS

| DE | 33 28 971 A1 | 2/1985 |
| EP | 0 406 887 A | 1/1991 |
| EP | 0 529 598 A | 3/1993 |
| EP | 1 366 754 A | 12/2003 |

OTHER PUBLICATIONS

STIC Search dated Dec. 4, 2009.*
International Search Report from corresponding PCT Application No. PCT/FR2006/000953 dated Sep. 5, 2006.

* cited by examiner

*Primary Examiner* — Eisa B Elhilo
(74) *Attorney, Agent, or Firm* — Finnegan, Henderson, Farabow, Garrett & Dunner LLP

(57) ABSTRACT

The invention relates to a keratin fiber dyeing composition comprising, in a suitable medium, at least one dye that is selected from among direct dyes and dye precursors, said cosmetic medium containing water and at least one propylene glycol derivative having formula $R_1(OC_3H_6)_nOR_2$ (I). The inventive composition can be used to obtain strong color while retaining the softness of the treated hair.

20 Claims, No Drawings

DYEING COMPOSITION COMPRISING A DYE AND A PROPYLENE GLYCOL DERIVATIVE

CROSS REFERENCE TO RELATED APPLICATIONS

This application is a national phase application based on PCT/FR2006/000953, filed on Apr. 27, 2006, and claims the benefit of U.S. Provisional Application No. 60/678,205, filed on May 6, 2005, and the priority of French Patent Application No. 0551084, filed Apr. 27, 2005, all of which are incorporated herein by reference in their entirety.

One subject of the invention is a dyeing composition comprising, in a medium suitable for dyeing keratinous fibers, at least one dye and a propylene glycol derivative, and also the process for dyeing keratinous fibers, in particular human keratinous fibers, using this composition.

For a long time, many people have sought to modify the color of their hair and in particular to mask their white hairs. In order to do this, several technologies have been developed.

It is known to dye keratinous substances, and in particular human hair, with dyeing compositions containing direct dyes. The conventional dyes which are used are, in particular, dyes of the nitrobenzene, anthraquinone, nitropyridine, azo, azo, xanthene, acridine, azine or triarylmethane type or natural dyes. These dyes may be nonionic, anionic, cationic or amphoteric.

These dyes, which are colored and coloring molecules that have an affinity for the keratinous fibers, are applied for the time required to obtain the desired coloring, then rinsed.

The colorings which result therefrom are particularly chromatic colorings which are however temporary or semipermanent as the nature of the interactions which bind the direct dyes to the keratinous fiber, and their desorption from the surface and/or from the core of the fiber are responsible for their low dyeability and their poor resistance to washing or to perspiration.

Furthermore, it is known to dye keratinous fibers permanently via oxidation dyeing. This dyeing technique consists in applying, to the keratinous fibers, a composition comprising dye precursors such as oxidation bases and couplers. These precursors, under the action of an oxidizer, will form one or more colored species in the hair.

The variety of molecules used as oxidation bases and couplers makes it possible to obtain a rich palette of colors. The colorings which result therefrom are permanent, powerful and resistant to exterior agents, especially to light, bad weather, washing, perspiration and rubbing. However, this type of dyeing leads to a degradation of the fiber due to the use of an oxidizer.

There is still a need to develop novel direct dyeing compositions in order to obtain varied hues, in particular pastel hues, which have a good resistance, especially to exterior agents such as light, shampoo or sweat. In particular, there is a need to develop dyeing compositions that make it possible to obtain colorings that have a resistance similar to that of oxidation dyeing without the drawbacks linked to the presence of an oxidizer.

Furthermore, there is a need to develop novel compositions for dyeing keratinous fibers that make it possible to extend the range of dyes which may be used, for example by improving the solubilization of some of these dyes so as to render them useable for dyeing keratinous fibers, in particular human keratinous fibers.

This objective is achieved by the present invention, one subject of which is a dyeing composition comprising, in a suitable medium, at least one dye chosen from direct dyes and dye precursors, the suitable medium containing water and at least one propylene glycol derivative of formula (I) below:

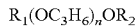

in which $R_1$ represents hydrogen, a $C_1$-$C_6$ alkyl radical or a $C_2$-$C_6$ acyl radical, $R_2$ represents a $C_2$-$C_6$ alkyl radical or a $C_6$-$C_{30}$ aryl radical and n varies from 1 to 6, the unit $OC_3H_6$ possibly being linear or branched.

This composition makes it possible, in particular, to obtain intense colorings, in varied hues, while preserving a good quality of the dyed keratinous fiber, in particular a soft feel. In addition, it allows the use of a wider range of dyes and/or the use of these dyes in larger amounts by increasing the dissolving power of the medium.

A second subject of the present invention relates to a process for dyeing keratinous fibers, in particular human keratinous fibers, using the composition of the invention.

Another subject of the present invention relates to the use of this composition for dyeing keratinous substances, in particular keratinous fibers such as the hair.

A final subject of the invention is a dyeing kit comprising, on the one hand, a composition that comprises a dye as defined previously and a propylene glycol derivative of formula (I) and, on the other hand, a composition containing an oxidizer.

The direct dyes that can be used in the composition of the invention are dyes that are soluble in water or in a solvent medium. By way of direct dye, mention may be made of neutral, acidic or cationic nitrobenzene direct dyes, neutral, acidic or cationic azo direct dyes, neutral, acidic or cationic quinone, and in particular anthraquinone, direct dyes, azine direct dyes, triarylmethane direct dyes, indoamine direct dyes and natural direct dyes.

Among the benzene direct dyes, mention may be made, nonlimitingly, of the following compounds:
- 1,4-diamino-2-nitrobenzene;
- 1-amino-2-nitro-4-β-hydroxyethylaminobenzene;
- 1-amino-2-nitro-4-bis(β-hydroxyethyl)aminobenzene;
- 1,4-bis(β-hydroxyethylamino)-2-nitrobenzene;
- 1-hydroxyethylamino-2-nitro-4-bis(β-hydroxyethyl-amino)benzene;
- 1-hydroxyethylamino-2-nitro-4-aminobenzene;
- 1-β-hydroxyethylamino-2-nitro-4-(ethyl)(β-hydroxyethyl) aminobenzene;
- 1-amino-3-methyl-4-β-hydroxyethylamino-6-nitrobenzene;
- 1-amino-2-nitro-4-β-hydroxyethylamino-5-chlorobenzene;
- 1,2-diamino-4-nitrobenzene;
- 1-amino-2-β-hydroxyethylamino-5-nitrobenzene;
- 1,2-bis(β-hydroxyethylamino)-4-nitrobenzene;
- 1-amino-2-tris(hydroxymethyl)methylamino-5-nitrobenzene;
- 1-hydroxy-2-amino-5-nitrobenzene;
- 1-hydroxy-2-amino-4-nitrobenzene;
- 1-hydroxy-3-nitro-4-aminobenzene;
- 1-hydroxy-2-amino-4,6-dinitrobenzene;
- 1-β-hydroxyethyloxy-2-β-hydroxyethylamino-5-nitrobenzene;
- 1-methoxy-2-β-hydroxyethylamino-5-nitrobenzene;
- 1-β-hydroxyethyloxy-3-methylamino-4-nitrobenzene;
- 1-β-dihydroxypropyloxy-3-methylamino-4-nitrobenzene;
- 1-β-hydroxyethylamino-4-β,γ-dihydroxypropyloxy-2-nitrobenzene;.
- 1-β,γ-dihydroxypropylamino-4-trifluoromethyl-2-nitrobenzene;
- 1-β-hydroxyethylamino-4-trifluoromethyl-2-nitrobenzene;

-1-β-hydroxyethylamino-3-methyl-2-nitrobenzene;
-1-β-aminoethylamino-5-methoxy-2-nitrobenzene;
-1-hydroxy-2-chloro-6-ethylamino-4-nitrobenzene;
-1-hydroxy-2-chloro-6-amino-4-nitrobenzene;
-1-hydroxy-6-bis(β-hydroxyethyl)amino-3-nitrobenzene;
-1-β-hydroxyethylamino-2-nitrobenzene; and
-1-hydroxy-4-β-hydroxyethylamino-3-nitrobenzene.

Among the azo direct dyes, mention may be made of the cationic azo dyes described in Patent Applications WO 95/15144, WO 95/01772 and EP-714 954, FR 2822696, FR 2825702, FR 2825625, FR 2822698, FR 2822693, FR 2822694, FR 2829926, FR 2807650, WO 02/78660, WO 02/100834, WO 02/100369, FR 3955369, the content of which forms an integral part of the invention.

Among these compounds, mention may most particularly be made of the following dyes:
-1,3-dimethyl-2-[[4-(dimethylamino)phenyl]azo]-1H-imidazolium chloride;
-1,3-dimethyl-2-[(4-aminophenyl)azo]-1H-imidazolium chloride; and
-1-methyl-4-[(methylphenylhydrazono)methyl]-pyridinium methyl sulfate.

Mention may also be made, among the azo direct dyes, of the following dyes, described in the Colour Index International, 3rd edition:
Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow-23, Acid Orange 24, Disperse Black 9.

Mention may also be made of 1-(4'-aminodiphenylazo)-2-methyl-4-bis(β-hydroxyethyl)aminobenzene and 4-hydroxy-3-(2-methoxyphenylazo)-1-naphthalenesulfonic acid.

Among the quinone direct dyes, mention may be made of the following dyes:
Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds:
-1-N-methylmorpholiniumpropylamino-4-hydroxyanthraquinone;
-1-aminopropylamino-4-methylaminoanthraquinone;
-1-aminopropylaminoanthraquinone;
-5-β-hydroxyethyl-1,4-diaminoanthraquinone;
-2-aminoethylaminoanthraquinone; and
-1,4-bis(β,γ-dihydroxypropylamino)anthraquinone.

Among the azine dyes, mention may be made of the following compounds:
Basic Blue 17 and Basic Red 2.

Among the triarylmethane dyes, mention may be made of the following compounds:
Basic Green 1, Acid Blue 9, Basic Violet 3, Basic Violet 14, Basic Blue 7, Acid Violet 49, Basic Blue 26, Acid Blue 7. Among the indoamine dyes, mention may be made of the following compounds:
-2-β-hydroxyethylamino-5-[bis(β-4'-hydroxyethyl)amino]anilino-1,4-benzoquinone;
-2-β-hydroxyethylamino-5-(2'-methoxy-4'-amino)anilino-1,4-benzoquinone;
-3-N-(2'-chloro-4'-hydroxy)phenylacetylamino-6-methoxy-1,4-benzoquinone imine;
-3-N-(3'-chloro-4'-methylamino)phenylureido-6-methyl-1,4-benzoquinone imine; and
-3-[4'-N-(ethyl,carbamylmethyl)amino]phenylureido-6-methyl-1,4-benzoquinone imine.

Among the direct dyes, mention may also be made of natural direct dyes such as lawsone, juglone, alizarine, purpurin, carminic acid, kermesic acid, purpurogallin, protocatechualdehyde, indigo, isatin, curcumin, spinulosin, apigenidin. It is also possible to use extracts or decoctions containing these natural dyes and especially cataplasms or extracts based on henna.

The direct dye or dyes present in the composition of the invention may be present in an amount generally between around 0.001 and 20% by weight of the total weight of the composition and preferably from around 0.001 to 5% by weight.

The dye precursors that can be used in the present invention are, for example, the oxidation bases and couplers conventionally used for oxidation dyeing.

By way of example, the oxidation bases may be chosen from para-phenylenediamines, bisphenylalkylenediamines, para-aminophenols, bis-para-aminophenols, ortho-aminophenols, heterocyclic bases and addition salts thereof.

Among the para-phenylenediamines, mention may be made of para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl,β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 4-aminophenylpyrrolidine, 2-thienyl-para-phenylene-diamine, 2-(β-hydroxyethylamino)-5-aminotoluene, 3-hydroxy-1-(4'-aminophenyl)pyrrolidine, and their addition salts with an acid.

Among the para-phenylenediamines cited above, para-phenylenediamine, para-toluenediamine, 2-isopropyl-para-phenylenediamine, 2-(β-hydroxyethyl)-para-phenylenediamine, 2-(β-hydroxyethyloxy)-para-phenylene-diamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine, and their addition salts with an acid are particularly preferred.

Among the bisphenylalkylenediamines, mention may be made, by way of example, of N,N'-bis(β-hydroxyethyl)-N,N'-bis(4'-aminophenyl)-1,3-diaminopropanol, N,N'-bis-(β-hydroxyethyl)-N,N'-bis(4'-aminophenyl)-ethylenediamine, N,N'-bis(4-aminophenyl)tetramethylene-diamine, N,N'-bis (β-hydroxyethyl)-N,N'-bis(4-amino-phenyl)tetramethylene-diamine, N,N'-bis(4-methyl-aminophenyl)tetramethylenediamine, N,N'-bis(ethyl)-N,N'-bis(4'-amino-3'-methylphenyl) ethylenediamine, 1,8-bis(2,5-diaminophenoxy)-3,6-dioxaoctane, and their addition salts with an acid.

Among the para-aminophenols, mention may be made, by way of example, of para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)-phenol, 4-amino-2-(aminomethyl)phenol, 4-amino-2-((β-hydroxyethyl)aminomethyl)phenol, 4-amino-2-fluorophenol, and their addition salts with an acid.

Among the ortho-aminophenols, mention may be made, by way of example, of 2-aminophenol, 2-amino-5-methylphenol, 2-amino-6-methylphenol, 5-acetamido-2-aminophenol, and their addition salts with an acid.

Among the heterocyclic bases, mention may be made, by way of example, of pyridine derivatives, pyrimidine derivatives and pyrazole derivatives.

Among the pyridine derivatives, mention may be made of the compounds described, for example, in Patents GB 1 026 978 and GB 1 153 196, such as 2,5-diaminopyridine, 2-[(4-methoxyphenyl)amino]-3-amino-pyridine, 2,3-diamino-6-methoxypyridine, 2-[(β-methoxy-ethyl)amino]-3-amino-6-methoxypyridine, 3,4-diamino-pyridine, and their addition salts with an acid.

Other pyridine oxidation bases that can be used in the present invention are the 3-aminopyrazolo[1,5-a]pyridine oxidation bases or their addition salts described, for example, in Patent Application FR 2801308. By way of example, mention may be made of pyrazolo[1,5-a]pyridin-3-ylamine; 2-acetylamino-pyrazolo[1,5-a]pyridin-3-ylamine; 2-morpholin-4-yl-pyrazolo[1,5-a]pyridin-3-ylamine; 3-aminopyrazolo[1,5-a]pyridine-2-carboxylic acid; 2-methoxypyrazolo[1,5-a]pyridin-3-ylamino; (3-aminopyrazolo[1,5-a]pyridin-7-yl)methanol; 2-(3-aminopyrazolo[1,5-a]pyridin-5-yl)ethanol; 2-(3-aminopyrazolo[1,5-a]pyridin-7-yl)ethanol; (3-aminopyrazolo[1,5-a]pyridin-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyridin-3-ylamine; pyrazolo[1,5-a]pyridine-3,5-diamine; 5-morpholin-4-ylpyrazolo[1,5-a]pyridin-3-ylamine; 2-[(3-aminopyrazolo[1,5-a]pyridin-5-yl)-(2-hydroxyethyl)amino]ethanol; 2-[(3-aminopyrazolo[1,5-a]-pyridin-7-yl)-(2-hydroxyethyl)amino]ethanol; 3-amino-pyrazolo[1,5-a]pyridin-5-ol; 3-aminopyrazolo[1,5-a]-pyridin-4-ol; 3-aminopyrazolo[1,5-a]pyridin-6-ol; 3-aminopyrazolo[1,5-a]pyridin-7-ol; and also their addition with an acid or with a base.

Among the pyrimidine derivatives, mention may be made of the compounds described, for example, in Patents DE 2359399; JP 88 169571; JP 05-63124; EP 0 770 375 or Patent Application WO 96/15765 such as 2,4,5,6-tetra-aminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and pyrazolopyrimidine derivatives such as those mentioned in Patent Application FR A 2750048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo-[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)-amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine and their addition salts with an acid and their tautomeric forms, when there is a tautomeric equilibrium.

Among the pyrazole derivatives, mention may be made of the compounds described in Patents DE 3843892, DE 4133957 and Patent Applications WO 94/08969, WO 94/08970, FR-A-2 733 749 and DE 195 43 988 such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)-amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)-amino-1-methylpyrazole, and their addition salts with an acid.

The oxidation base or bases present in the composition of the invention are generally each present in an amount between around 0.001 to 10% by weight of the total weight of the dyeing composition, preferably between 0.005 and 6%.

The couplers that can be used in the composition of the invention are, for example, meta-phenylenediamine couplers, meta-aminophenol couplers, meta-diphenol couplers, naphthalene couplers, heterocyclic couplers and addition salts thereof.

By way of example, mention may be made of 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and their addition salts with an acid.

In the composition of the present invention, the coupler or couplers are each generally present in an amount between around 0.001 and 10% by weight of the total weight of the dyeing composition, preferably between 0.005 and 6%.

The composition of the invention may of course comprise, in combination with direct dyes, oxidation bases and couplers.

In the composition of the invention, for the propylene glycol derivative of formula (I), the expression "alkyl radical" is understood to mean linear or branched radicals such as the methyl, ethyl, propyl, isopropyl, isobutyl, tert-butyl, pentyl or hexyl radical. By way of aryl radical, mention may especially be made of phenyl or benzyl radicals.

In the formula (I), the unit $OC_3H_6$ represents, for example, $OCH_2CH_2CH_2$, $OCH_2CH(CH_3)$ or $OCH(CH_3)CH_2$.

As propylene glycol derivatives of formula (I), mention may be made of the following propylene glycols:

| Name | Chemical formula |
|---|---|
| Dipropylene glycol n-propyl ether (DPnP) | $C_3H_7O[CH_2(CH)CH_3O]_2H$ |
| Tripropylene glycol n-propyl ether (TPnP) | $C_3H_7O[CH_2(CH)CH_3O]_3H$ |
| Dipropylene glycol n-butyl ether (DPnB) | $C_4H_9O[CH_2(CH)CH_3O]_2H$ |
| Tripropylene glycol n-butyl ether (TPnB) | $C_4H_9O[CH_2(CH)CH_3O]_3H$ |
| Propylene glycol n-butyl ether | |
| Propylene glycol n-propyl ether | |

According to one particular embodiment, the propylene glycol derivative of formula (I) is such that n is between 2 and 4 inclusive and $R_2$ represents a linear or branched ethyl, propyl or butyl radical.

The composition of the invention generally comprises an amount of propylene glycol derivative of formula I between 0.1 and 80%, preferably between 0.5 and 50% and even more preferably between 1 and 30% of the total weight of the composition.

Preferably, the amount of water is at least equal to 40% relative to the total weight of the dyeing composition. Even more preferably, this amount of water is at least equal to 70%.

According to one particular embodiment, the medium suitable for dyeing keratinous fibers comprises at least 70% water by weight relative to the total weight of the composition. It may, for example, be composed solely of water or of a mixture of water and at least one organic solvent other than the propylene glycol derivative of formula (I). As an additional organic solvent, mention may, for example, be made of the $C_1$-$C_4$ lower alkanols, such as ethanol and isopropanol; polyols and polyol ethers such as 2-butoxyethanol, diethylene glycol monoethyl ether and monomethyl ether, and also aromatic alcohols such as benzyl alcohol or phenoxyethanol, and mixtures thereof.

For dyeing human keratinous fibers, the dyeing medium is a cosmetically suitable medium.

The total amount of solvent including the propylene glycol derivative or derivatives of formula (I) may vary between around 0.1 and 80% by weight relative to the total weight of the composition, and more preferably between around 0.5 and 50% by weight and even more preferably between 1 and 30% of the total weight of the composition.

The dyeing composition according to the invention may also incorporate various adjuvants conventionally used in compositions for dyeing hair, such as anionic, cationic, nonionic, amphoteric or zwitterionic surfactants or mixtures thereof, anionic, cationic, nonionic, amphoteric or zwitterionic polymers or mixtures thereof, mineral or organic thickening agents, and in particular anionic, cationic, nonionic and amphoteric polymeric associative thickeners, antioxidants, penetrating agents, sequestering agents, fragrances, buffers, dispersants, conditioning agents such as, for example, volatile or nonvolatile, modified or unmodified silicones, film-forming agents and in particular nonionic, cationic, anionic or amphoteric fixing polymers, ceramides, preservatives and opacifiers.

The above adjuvants are generally present in an amount between, for each of them, 0.01 and 20% by weight relative to the weight of the composition.

Of course, a person skilled in the art will be sure to choose this or these optional adjuvants so that the advantageous properties intrinsically linked to the composition according to the invention are not, or are not substantially, impaired by the envisaged addition or additions.

The pH of the dyeing composition according to the invention is generally between around 2 and 12. When the composition comprises, by way of dye, dye precursors then the pH is preferably between 8 and 12.

It may be adjusted to the desired value using acidifying or basifying agents commonly used in dyeing keratinous fibers or else using conventional buffer systems.

Among the acidifying agents, mention may be made, by way of example, of mineral or organic acids such as hydrochloric acid, orthophosphoric acid, sulfuric acid, carboxylic acids such as acetic acid, tartaric acid, citric acid, lactic acid, and sulfonic acids.

Among the basifying agents, mention may be made, by way of example, of ammonia, alkali metal carbonates, alkanolamines such as mono-, di- and triethanolamines and also derivatives thereof, sodium or potassium hydroxides and compounds of formula (III) below:

(III)

in which W is a propylene residue optionally substituted by a hydroxyl group or a $C_1$-$C_4$ alkyl radical; $R_6$, $R_7$, $R_8$ and $R_9$, being identical or different, represent a hydrogen atom, a $C_1$-$C_4$ alkyl radical or a $C_1$-$C_4$ hydroxyalkyl radical.

The dyeing composition according to the invention may be in various forms, such as in the form of liquids, creams, gels or any other appropriate form for carrying out dyeing of keratinous fibers, and especially of human hair.

Another subject of the invention is a process for dyeing keratinous fibers which comprises the application of the composition of the invention as defined previously to the keratinous fibers for a sufficient time to obtain the desired coloring. The keratinous fibers are then rinsed. The leave-in time is generally between around 1 to 60 minutes, preferably around 5 to 60 minutes.

The composition of the invention may, in addition, comprise an oxidizer.

When the composition of the invention only contains direct dyes, this oxidizer makes it possible to obtain a lightening dyeing, that is to say a simultaneous bleaching and dyeing of the hair.

When the dyeing composition comprises an oxidation base and/or a coupler, it is necessary to bring this composition into contact with an oxidizer in order to form the dyeing composition may then contain an oxidizer. The oxidizers conventionally used for oxidation dyeing of keratinous fibers are, for example, hydrogen peroxide, urea peroxide, alkali metal bromates, persalts such as perborates and persulfates, peracids and oxidase enzymes, among which mention may be made of peroxidases, 2-electron oxidoreductases such as uricases and 4-electron oxygenases such as laccases. Hydrogen peroxide is particularly preferred.

The oxidizer may be added to the composition of the invention just at the time of use or it may be carried out using an oxidizing composition containing it, this composition being applied simultaneously or sequentially to the composition of the invention. The oxidizing composition may also incorporate various adjuvants conventionally used in compositions for dyeing hair and as defined previously.

The pH of the oxidizing composition incorporating the oxidizer is such that after mixing with the dyeing composition, the pH of the resulting composition applied to the keratinous fibers preferably varies between around 3 and 12, and even more preferably between 5 and 11. It may be adjusted to the desired value using acidifying or basifying agents commonly used in dyeing keratinous fibers and as defined previously.

The composition which is finally applied to the keratinous fibers may be in various forms, such as in the form of liquids, creams, gels or any other suitable form for carrying out dyeing of keratinous fibers, and especially of human hair.

The dyeing process may be carried out at ambient temperature or at higher temperatures, for example using a hair dryer, a hood dryer, a straightening iron, etc.

The examples which follow are used to illustrate the invention without however being limiting.

EXAMPLES

Example 1

The following composition was prepared:

| | |
|---|---|
| p-aminophenol | $5 \times 10^{-3}$ moles |
| 2-methyl-5-aminophenol | $5 \times 10^{-3}$ moles |
| Dyeing medium (*) | qs for 100 g |

Dyeing medium (*)
10% dipropylene glycol n-propyl ether;
10% of a 20% aqueous solution of ammonia; and
80% water.

This composition was mixed, weight for weight, at the time of use with 20-volume hydrogen peroxide, then the mixture was applied to a lock of natural hair containing 90% of white hair and also to a lock of permed hair containing 90% of white hair. The locks were then shampooed, rinsed and then dried. The locks thus treated had a strong and homogeneous copper coloring and were soft to touch.

Example 2

A direct dyeing composition was obtained from the dye Acid Orange 7 at 0.5% in a mixture composed of 4% tripropylene glycol n-propyl ether and of 96% water acidified by citric acid (qs for pH 2.7).

This composition was then applied for 20 minutes to a lock of natural hair containing 90% of white hair and also to a lock of permed hair containing 90% of white hair. After rinsing and drying, the locks were dyed orange in a strong and attractive manner.

Example 3

A direct dyeing composition was obtained from the dye 1-(beta-hydroxyethylamino)-2-nitro-4-aminobenzene at 0.6% in a mixture composed of 4% tripropylene glycol n-propyl ether and 96% water.

The composition was then applied for 20 minutes to a lock of natural hair containing 90% of white hair and also to a lock of permed hair containing 90% of white hair. After rinsing and drying, the locks were dyed dark purple-red in an intense and attractive manner.

The invention claimed is:

1. A dyeing composition comprising, in a medium suitable for dyeing keratinous fibers, at least one dye chosen from at least one direct dye and at least one dye precursor, said medium comprising water and at least one propylene glycol derivative of formula (I) below:

$$R_1(OC_3H_6)_nOR_2 \quad (I)$$

wherein
$R_1$ is chosen from hydrogen, linear or branched $C_1$-$C_6$ alkyl radicals, and linear or branched $C_2$-$C_6$ acyl radicals;
$R_2$ is chosen from linear or branched $C_2$-$C_6$ alkyl radicals;
n is chosen from integers ranging from 1 to 6; and
the unit $OC_3H_6$ being linear or branched.

2. The composition according to claim 1, wherein the at least one direct dye is chosen from neutral nitrobenzene direct dyes; acidic nitrobenzene direct dyes; cationic nitrobenzene direct dyes; neutral azo direct dyes; acidic azo direct dyes; cationic azo direct dyes; neutral quinone direct dyes; acidic quinone direct dyes; cationic quinone direct dyes; azine direct dyes; triarylmethane direct dyes; indoamine direct dyes; and natural direct dyes.

3. The composition according to claim 1, wherein the at least one direct dye is present in the composition in an amount ranging from about 0.001 to 20% by weight of the total weight of the composition.

4. The composition according to claim 1, wherein the at least one dye precursor is at least one oxidation base chosen from para-phenylenediamines, bisphenylalkylenediamines, para-aminophenols, bis-para-aminophenols, ortho-aminophenols, heterocyclic bases, and addition salts thereof.

5. The composition according to claim 4, wherein the at least one oxidation base is present in an amount ranging from about 0.001 to 10% by weight of the total weight of the dyeing composition.

6. The composition according to claim 4, wherein the at least one oxidation base is present in an amount ranging from about 0.005% to 6% by weight of the total weight of the dyeing composition.

7. The composition according to claim 1, wherein the at least one dye precursor is at least one coupler chosen from meta-phenylenediamine couplers, meta-aminophenol couplers, meta-diphenol couplers, naphthalene couplers, heterocyclic couplers, and addition salts thereof.

8. The composition according to claim 7, wherein the at least one coupler is present in an amount ranging from about 0.001% to 10% by weight of the total weight of the composition.

9. The composition according to claim 1, wherein, in the at least one propylene glycol derivative of formula (I), n is an integer ranging from 2 to 4.

10. The composition according to claim 1, wherein $R_2$ is chosen from ethyl radicals, linear or branched propyl radicals, and linear or branched butyl radicals.

11. The composition according to claim 1, wherein the amount of the at least one propylene glycol derivative of formula (I) ranges from 0.1% to 40% of the total weight of the composition.

12. The composition according to claim 1, wherein the amount of the at least one propylene glycol derivative of formula (I) ranges from 1% to 20% of the total weight of the composition.

13. The composition according to claim 1, wherein the at least one propylene glycol derivative of formula (I) is chosen from dipropylene glycol n-propyl ether, tripropylene glycol n-propyl ether, dipropylene glycol n-butyl ether, tripropylene glycol n-butyl ether, propylene glycol n-butyl ether, and propylene glycol n-propyl ether.

14. The composition according to claim 1, wherein the amount of water is at least 40% by weight of the total weight of the composition.

15. The composition according to claim 14, wherein the medium suitable for dyeing keratinous fibers comprises at least 70% water by weight relative to the total weight of the composition.

16. The composition according to claim 1, further comprising at least one component chosen from anionic surfactants, cationic surfactants, nonionic surfactants, amphoteric surfactants, zwitterionic surfactants; anionic polymers, cationic polymers, nonionic polymers, amphoteric polymers, zwitterionic polymers; thickening agents chosen from mineral thickening agents and organic thickening agents; antioxidants; penetrating agents; sequestering agents; fragrances; buffers; dispersants; conditioning agents; film-forming agents; ceramides; preservatives; and opacifiers.

17. The composition according to claim 16, wherein the thickening agents are chosen from anionic polymeric associative thickeners, cationic polymeric associative thickeners, nonionic polymeric associative thickeners, and amphoteric polymeric associative thickeners; the conditioning agents are chosen from volatile silicones, nonvolatile silicones, modified silicones, and unmodified silicones; and the film-forming agents are chosen from nonionic fixing polymers, cationic fixing polymers, anionic fixing polymers, and amphoteric fixing polymers.

18. The composition according to claim 1, further comprising at least one oxidizer.

19. A process for dyeing keratinous fibers comprising:
(a) applying to keratinous fibers for a sufficient time to obtain the desired coloring, an effective amount of a composition, wherein the composition comprises, in a medium suitable for dyeing keratinous fibers, at least one dye chosen from at least one direct dye and at least one dye precursor, said medium comprising water and at least one propylene glycol derivative of formula (I) below:

$$R_1(OC_3H_6)_nOR_2 \quad (I)$$

wherein
$R_1$ is chosen from hydrogen, linear or branched $C_1$-$C_6$ alkyl radicals, and linear or branched $C_2$-$C_6$ acyl radicals;
$R_2$ is chosen from linear or branched $C_2$-$C_6$ alkyl radicals;
n is chosen from integers ranging from 1 to 6; and
the unit $OC_3H_6$ being linear or branched;
(b) rinsing the keratinous fibers.

20. A dyeing kit comprising:
(a) a dyeing composition, wherein the dyeing composition comprises, in a medium suitable for dyeing keratinous fibers, at least one dye chosen from at least one direct dye and at least one dye precursor, said medium comprising water and at least one propylene glycol derivative of formula (I) below:

$$R_1(OC_3H_6)_nOR_2 \quad (I)$$

wherein
$R_1$ is chosen from hydrogen, linear or branched $C_1$-$C_6$ alkyl radicals, and linear or branched $C_2$-$C_6$ acyl radicals;
$R_2$ is chosen from linear or branched $C_2$-$C_6$ alkyl radicals;
n is chosen from integers ranging from 1 to 6; and
the unit $OC_3H_6$ being linear or branched; and
(b) optionally a composition containing at least one oxidizer.

* * * * *